US009765313B2

(12) United States Patent
Yao et al.

(10) Patent No.: US 9,765,313 B2
(45) Date of Patent: Sep. 19, 2017

(54) METHOD FOR PRODUCING A PHYTASE VARIANT WITH IMPROVED THERMAL STABILITY, AND A PHYTASE VARIANT AND THE USE THEREOF

(71) Applicant: FEED RESEARCH INSTITUTE, Beijing (CN)

(72) Inventors: Bin Yao, Beijing (CN); Huoqing Huang, Beijing (CN); Huiying Luo, Beijing (CN); Chao Shao, Beijing (CN); Yingguo Bai, Beijing (CN); Yaru Wang, Beijing (CN); Peilong Yang, Beijing (CN); Pengjun Shi, Beijing (CN); Kun Meng, Beijing (CN); Heng Zhao, Beijing (CN); Rui Ma, Beijing (CN)

(73) Assignee: Feed Research Institute, Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 15/112,198

(22) PCT Filed: Nov. 12, 2013

(86) PCT No.: PCT/CN2013/086943
§ 371 (c)(1),
(2) Date: Jul. 18, 2016

(87) PCT Pub. No.: WO2015/070372
PCT Pub. Date: May 21, 2015

(65) Prior Publication Data
US 2017/0022486 A1    Jan. 26, 2017

(51) Int. Cl.
C12N 9/16 (2006.01)
C12N 15/63 (2006.01)
(Continued)

(52) U.S. Cl.
CPC .............. C12N 9/16 (2013.01); A23K 20/189 (2016.05); C12N 1/14 (2013.01); C12N 1/20 (2013.01);
(Continued)

(58) Field of Classification Search
None
See application file for complete search history.

(56) References Cited

U.S. PATENT DOCUMENTS

2003/0103958 A1* 6/2003 Short .................. A23L 11/33
424/94.6
2006/0141562 A1* 6/2006 Blattmann .............. C12N 9/16
435/69.1
(Continued)

*Primary Examiner* — Robert Mondesi
*Assistant Examiner* — Richard Ekstrom
(74) *Attorney, Agent, or Firm* — PatShegen IP

(57) ABSTRACT

The present invention relates to the field of genetic engineering, in particular, the present invention relates to a method for producing a phytase variant with an improved thermal stability, and a phytase variant and the use thereof. The phytase variant contains at least one proline modification, compared to the phytase from *Escherichia coli* and other mutants thereof. The phytase variants with the modification have preferably improved properties, such as the thermal stability, optimal reaction temperature, pH property, specific activity, protease resistance and performance in animal feeds.

11 Claims, 1 Drawing Sheet

(51) Int. Cl.
*C12N 1/20* (2006.01)
*C12N 1/14* (2006.01)
*C12N 15/52* (2006.01)
*A23K 20/189* (2016.01)

(52) U.S. Cl.
CPC ............ *C12N 15/52* (2013.01); *C12N 15/63* (2013.01); *C12Y 301/03* (2013.01)

(56) References Cited

U.S. PATENT DOCUMENTS

| | | | |
|---|---|---|---|
| 2010/0068335 A1* | 3/2010 | Lei ............................ | C12N 9/16 426/2 |
| 2013/0122567 A1* | 5/2013 | Blesa ....................... | C12N 9/16 435/196 |
| 2014/0242249 A1* | 8/2014 | Nguyen ................... | C12N 9/16 426/588 |

* cited by examiner

SEQUENCE LISTING

<160> NUMBER OF SEQ ID NOS: 2

<210> SEQ ID NO 1
<211> LENGTH: 1233
<212> TYPE: DNA
<213> ORGANISM: Escherichia coli

<400> SEQUENCE: 1

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
taccaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagctga cacttcttct     360
ccagatccat tgttcaaccc tttgaagact ggtgttttgcc aattggacaa cgctaacgtt     420
actgacgcta tcttgtccag agctggagga tccattgctg acttcaccgg tcacagacag     480
actgccttca gagagttgga aagagttctt aacttcccac aatccaactt gtgccttaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tctacttgct gcagagaact     780
ccagaggttg ctagatccag agccaccccca ttgttggact tgatcaagac tgctttgact     840
cctcacccac tcaaaagca agcctacggt gttaccttgc ccacttctgt cttgttcatt     900
gccggtcacg atactaactt ggcaaatctc ggcggtgctt tggagttgaa ctggactctt     960
cctggtcaac tgataacac tccaccaggt ggtgagctcg ttttcgaaag atggcgtaga    1020
ctatctgata actctcaatg gattcaggtt tcgttggtct tccaaacttt gcagcagatg    1080
agagacaaga ctccactgtc tttgaacacg cctccaggag aagtcaaatt gaccttggct    1140
ggatgtgaag agagaaatgc tcagggtatg tgttccttgg ctggtttcac tcaaatcgtt    1200
aacgaagcta gaatcccagc ttgttccttg taa                                 1233
```

<210> SEQ ID NO 2
<211> LENGTH: 410
<212> TYPE: PRT
<213> ORGANISM: Escherichia coli

<400> SEQUENCE: 2

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
```

```
                    100                 105                 110
His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
            130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
            165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
            245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410
```

METHOD FOR PRODUCING A PHYTASE VARIANT WITH IMPROVED THERMAL STABILITY, AND A PHYTASE VARIANT AND THE USE THEREOF

FIELD OF THE INVENTION

The present invention relates to the field of genetic engineering, in particular, the present invention relates to a method for producing a phytase variant with an improved thermal stability, and a phytase variant and the use thereof.

BACKGROUND OF THE INVENTION

Phosphorous (P) is an essential dietary nutrient for growth. It was found in the conventional animal feed such as grain, oilseed meal, by-product from seed that a large quantities of phosphorous is in presence of phosphate covalently bonded in phytic acid molecule. However, non-ruminant animals such as fowls and pigs lack digestive enzymes for separating inorganic phosphorus from the phytic acid molecule, so that a coefficient of utilization of phosphorus is very low.

Incapability of utilizing the phytic acid for the non-ruminant animal results in extra cost incurred from the addition of inorganic phosphorus such as calcium dihydrogen phosphate and defluorinated phosphate, or animal products such as meat, bone meal, and fish meal. In addition, the phytic acid combines with several essential minerals, such as calcium, zinc, iron, magnesium and copper, preventing or inhibiting the absorption of the minerals in the digestive tract. Therefore, a large amount of undigested phytate phosphorous in animal feeds was excreted, increasing the ecological phosphorus burden to the environment.

Addition of microbial phytases as feed additive improved the bioavailability of phytic acid in the non-ruminant animal's feed, so as to decrease the addition of inorganic phosphorus, and reduce the amount of phosphorus excreted in poultry manner. Also, the phytase may be applied to produce the feed ingredient with the lower continent of Calcium-magnesium phytate.

In spite of the well-known benefits of use of phytase including addition to animals feed and human's food, it was surprising that a little phytase was widely accepted and applied to feed, and starch liquefaction and alcohol fermentation industry, due to the phytase's properties being incapable of meeting the requirement of the application environment. It was the most important properties including high specific activity, low optimal pH, High resistance to pepsin and trypsin, and thermostability for the phytase being applied to starch liquefaction as feed enzyme, since the phytase would be exposed to the increasing temperature, such as 70 to 95° C. during feed pelleting technologies, and 75 to 120° C. during starch liquefaction technology.

The gene sequence of the phytase appA from *Escherichia coli* was provided by Dassa et al. in 1990 (J. Bact. P5497-5500, 1990). The phytase appA has the improved specific activity which 30-40 times larger than that of *Aspergillus niger* phytase, but was limited in its wide application to feed and starch liquefaction due to its thermostability. Many mutations to *E. coli* phytase had been started in the different commercial order, based on its inherent characteristics. The order of the present invention is to provide a phytase with the modified and improved temperature characteristic, not limited to the thermostability and the optimal temperature in the embodiment.

Order of the Invention

One order of the present invention is to provide an alternative polypeptide (phytase) with phytase activity, and the nucleotide sequence encoding the said polypeptide. The phytase variant of the present invention has the modified or improved characteristics, such as stabilities including acid or alkali stability, thermal stability, steam stability, pelleting stability and/or protease stability, especially pepsin and trypsin stability, the optimal temperature, pH characteristic, specific activity, and performance in feed, comparing with the parental phytase.

SUMMARY OF THE INVENTION

One aspect of the present invention is to provide a phytase as the expression product of the mutant DNA sequence, and which is based on the *E. coli* phyase appA. According to an embodiment, the said phytase variant has at least 70% homology with the amino acid as set forth in SEQ ID NO: 2, and has at least one addition of one or more pralines at the sites of S80P (A), S151P (B), T161P (C), N176P (D), S187P (E), and A380P (F), compared with SEQ ID NO:2, wherein A referring to proline being introduce at the position 80, B referring to proline being introduce at the position 151, C referring to proline being introduce at the position 161, D referring to proline being introduce at the position 176, E referring to proline being introduce at the position 187, and F referring to proline being introduce at the position 380. According to the present invention, the proline$^{1st}$ is introduced at the $80^{th}$ site of Serine residue; the proline$^{2nd}$ is preferably introduced at the $151^{th}$ site of Serine residue; the proline$^{4th}$ is preferably introduced at the $176^{th}$ site of Asparagine residue; the proline$^{5th}$ is preferably introduced at the $187^{th}$ site of Serine residue; and the proline$^{6th}$ is preferably introduced at the $380^{th}$ site of Alanine residue.

According to the present invention, the term "the number of position" is referred to the number of position in SEQ ID NO: 2, and the term "Percent identity" is referred in the description of "Percent identity with the sequence of the phytase polypeptide".

According to an embodiment of the present invention, the amount of being introduced prolines are 2, 3, 4, 5, and/or 6, wherein A referring to S80P, B referring to S151P, C referring to T161P, D referring to N176P, E referring to S187P, and F referring to A380P.

In case of two prolines being introduced, A can be combined respectively with B, C, D, E, and F, B can be combined respectively with C, D, E, and F, C can be combined respectively with D, E, and F, D can be combined respectively with E, and F, and E can be combined with F.

In case of three prolines being introduced, the combination may A+B+C, A+B+D, A+B+E, A+B+F, A+C+D, A+C+E, A+C+F, A+D+E, A+D+F, A+E+F, B+C+D, B+C+E, B+C+F, B+D+E, B+D+F, B+E+F, B+E+G, C+D+E, C+D+F, C+E+F, or D+E+F In case of four prolines being introduced, the combination may be A+B+C+D, A+B+C+E, A+B+C+F, A+B+D+E, A+B+D+F, A+B+E+F, A+C+D+E, A+C+D+F, A+C+E+F, A+D+E+F, B+C+D+E, B+C+D+F, B+C+E+F, B+D+E+F, or C+D+E+F.

In case of five prolines being introduced, the combination may be A+B+C+D+E, A+B+C+D+F, A+B+C+E+F, A+B+D+E+F, A+C+D+E+F, or B+C+D+E+F.

In case of six prolines being introduced, the combination may be A+B+C+D+E+F.

According to the present invention, the method can produce the phytase variants with the improved characteristics, such as the thermal stability, the steam stability, the pelleting stability, the acid stability, pH characteristic, and/or protease stability, especially pepsin and trypsin stability, the optimal temperature, specific activity, the substrate specificity, the optimal temperature, and performance in feed such as the improved activity of releasing and/or hydrolysating phytate. The phytase variants of the present invention has the specially improved thermal characteristic, such as thermostability, the optimal temperature, the pelleting stability and or the improved activity in the animal feed.

Therefore, the present invention provides the phytase variants with the improved thermal characteristics such as thermostability, the optimal temperature, protease stability and/or the pelleting stability.

The present invention further provides the polynucleotides encoding the said phytase variants, the nucleotide constructions prepared by optionally connecting the said polynucleotides to one or more regulatory sequences guiding the said polypeptide being expressed in the expression host, recombinant expressing vector containing the said nucleotide constructions, and the recombinant host cell containing the said nucleotide constructions and/or the said recombinant expressing vector. Therefore, the present invention relates to the isolated DNA encoding the said phytase variants and the expression vector containing the said DNA.

The present invention relates to a method of producing the said phytase variants, including the steps:

(a) Cultivating the host cells to provide the supernatant containing the said phytase; and (b) Recovering the said phytase.

Another aspect of the invention is to provide phytase variants with the improved enzymic characteristics. According to embodiment, the said improved enzymic characteristic is the improved thermostability.

Yet another aspect of the invention is to provide a method of adding the said phytase variants to the animal feed to improve its nutritional value. Furthermore, another aspect of the invention is to provide enzyme composition of the proteins with the phytase activity, which may be commercially used. According to the embodiment of the present invention, the said enzyme composition is animal feed composition. In another embodiment, the said enzyme composition may be applied to starch hydrolysis process, such as the starch liquefaction technology.

DETAIL DESCRIPTION OF THE INVENTION

The method of the present invention may be applied to construct the variants of any wild type or mutant type phytase. According to the present invention, the term "phytase" refers to polypeptide with phytase activity of catalyzing the sequential hydrolysis of phytic acid to produce (1) inositol and/or (2) its derivatives and (3) inorganic phosphate.

According to the present invention, 1 unit of phytase activity was determined to be the enzyme amount for releasing 1 μmol of inorganic phosphate for 1 minute, at pH5.5 and 37° C.

According to the present invention, the term "identity" is referred to the identity value of the two polypeptide sequences comparing by software Align 10.0 of Vector NTI.

In the embodiment of the present invention, the phytase variants are at least about 70%, 71%, 72%, 73%, 74%, 75, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% homologous to the entire amino acid sequence as shown in SEQ ID NO: 2 of the present invention. And, in the further embodiment of the present invention, the homology is at least about 98.0%, 98.2%, 98.4%, 98.6%, 98.8%, 99.0%, 99.1%, 99.2%, 99.3%, 99.4%, 99.5%, 99.6%, 99.7%, 99.8%, or 99.9%. In the other embodiments, the homology is at least about 70%, 71%, 72%, or 73%.

According to the embodiment of the present invention, no more than 2, 3, 4, 5, 6, 7, 8, 9, or 10 amino acids are modified comparing with the sequence as set forth in SEQ ID NO:2 or the sequence of the parental phytase; no more than 11, 12, 13, 14, 15, 16, 17, 18, 19, or 20 amino acids are modified comparing with the sequence as set forth in SEQ ID NO:2 or the sequence of the parental phytase; no more than 21, 22, 23, 24, 25, 26, 27, 28, 29, or 30 amino acids are modified comparing with the sequence as set forth in SEQ ID NO:2 or the sequence of the parental phytase; no more than 31, 32, 33, 34, 35, 36, 37, 38, 39, or 40 amino acids are modified comparing with the sequence as set forth in SEQ ID NO:2 or the sequence of the parental phytase; no more than 41, 42, 43, 44, 45, 46, 47, 48, 49, or 50 amino acids are modified comparing with the sequence as set forth in SEQ ID NO:2 or the sequence of the parental phytase; no more than 51, 52, 33, 54, 55, 56, 57, 58, 59, or 60 amino acids are modified comparing with the sequence as set forth in SEQ ID NO:2 or the sequence of the parental phytase; no more than 61, 62, 63, 64, 65, 66, 67, 68, 69, or 70 amino acids are modified comparing with the sequence as set forth in SEQ ID NO:2 or the sequence of the parental phytase; no more than 71, 72, 73, 74, 75, 76, 77, 78, 79, or 80 amino acids are modified comparing with the sequence as set forth in SEQ ID NO:2 or the sequence of the parental phytase; no more than 81, 82, 83, 84, 85, 86, 87, 88, 89, or 90 amino acids are modified comparing with the sequence as set forth in SEQ ID NO:2 or the sequence of the parental phytase; or, no more than 91, 92, 93, 94, 95, 96, 97, 98, 99, or 100 amino acids are modified comparing with the sequence as set forth in SEQ ID NO:2 or the sequence of the parental phytase.

According to the present invention, the position of the amino acid is defined based on the amino acid sequence of the phytase from the *Escherichia coli* under the No. ABF60232 deposited in GenBank, having the sequence from the site 1 to 410 as set forth in EQ ID NO:2. Thus, the position referred hereto is from Q1(Gln1) to L410 (Leu410) based on the sequence of EQ ID NO:2.

According to the present invention, the term "mature sequence" refers to the residual polypeptide removing the signal peptide. Commonly, the first amino acid of the mature active protein can be determined by the N-terminus of the purified phytase. Thus, the N-terminus may be the amino acids translated by the restriction endonuclease of the secretory expression vector after being connected to the expression vector.

The modification to the phytase template set forth in SEQ ID NO: 2 may be substitution, deletion and/or insertion of one or more amino acid residues. In the present invention, the term "insertion" also includes N- or C-terminus extension. For example, it is remarked as "S80P" replacing the Serine at the position 80 with the proline.

No definition on the substitution or extension means insertion of any nature or unnatural amino acid except the amino acid locating the position of the template.

The phytase variants have the modified and improved characteristics. The term "modified" and "improved" means comparing with other phytase such as the wild type phytase in WO 2009/073399, the variant Nov9X in WO 2009/

073399, the phyase with SEQ ID NO:2 in WO 2008/036916 or the phyase with SEQ ID NO:4 in WO 2008/036916.

According to the present invention, the thermostability is determined by the remaining activity of the phytase relative to that prior incubating as described in the examples. The phytase variants have the remaining activity more than that of the control phytase, showing having the improved thermostability. The remaining activity of the phytase variants of the present invention is preferably 105% of the control phytase, more preferably 110%, 115%, 120%, 130%, 140%, 150%, 160%, 170%, 180%, 190% or at least 200 of the control phytase.

The optimal temperature of the phytase variants is determined as described in the examples, and the activity at each temperature is preferably normalized as the relative activity to that in the optimal temperature in the form of percentage.

The optimal pH of the phytase variants is determined as described in the examples, and the activity at each pH is preferably normalized as the relative activity to that in the optimal pH in the form of percentage.

The phytase variants have the improved specific activity in comparison with the control phytase. In particular, the specific activity of the phytase variants of the present invention is at least about 105%, 110%, 115%, 120%, 125%, 130%, 140%, 145%, 150%, 160%, 170%, 180%, 190%, or even 200% of that of the control phytase determined by the same method. Or, the term "high specific activity" refers to that the specific activity is at least 200 U/mg. The specific activity is measured with highly purified sample, being demonstrated by SDS-PAGE electrophoresis. The protein concentration may be measured with Bradford protein concentration measuring kit, and the unit of the phytase activity is showed as U as described in the examples. And, the specific activity (U) is the characteristic of the specific phytase, and calculated as the phytase activity per mg of phytase variants protein.

According to the present invention, the term "expression vector" is defined as DNA molecule in straight chain or circle, including the polynucleotide encoding the polypeptide of the preset invention, which may be optionally connected to the other polynucleotides providing its expression. The conventional expression vector includes promoter, ribosome binding sites, translation initiation signal, and optional repressor gene or regulating sequences of the several activators.

The recombinant vector carrying the phytase variant DNA may be any vector which is convenient to the DNA recombination, and choose according to its host cell. For example, the expression vectors pPIC9, pPICZaA or pGAPZaA is suitable to expression in *Pichia pastoris*.

According to the present invention, the term "expression host cell" includes the optimal host cell which is transformed, transfected, or transduced by the nucleotide constructor containing the polynucleotide of the present invention, and expresses the phytase variants of the present invention. Said recombinant expression vector is constructed to express the phytase protein in the prokaryotic or eukaryotic cells, such as bacteria such as *Escherichia coli*, yeast such as *Pichia pastoris, Aspergillus* such as *Trichoderma*, insect cell such as Sf9 cell or Bombyx Mori cell, or plant cell such as *Arabidopsis thaliana* cell or Maize cell. Thus, present invention relates to the recombinant cell transformed with said recombinant expression vector, including the prokaryotic or eukaryotic cells, more preferable the *Pichia pastoris* cell.

Said host cell of the present invention including the cultivated prokaryotic or eukaryotic cells may be applied to produce the phytase variants. Thus, the present invention relates to the method of producing phytase protein with the host cell of the present invention. According to the embodiment, said method including the steps of cultivating the host cells of the present invention transformed with said recombinant expression vector containing sequence encoding the phytase variants in the suitable medium under the suitable condition of phytase expression, and producing the phytase. Said method also includes the step of isolating the phytase from the medium or the host cell.

According to the embodiment of the present invention, the phytase variants of the present invention have the improved activity in the animal feed in comparison with the control phytase. The performance in the animal feed can be determined by the simulated assay in vitro. For example, according to the embodiment of the present invention, the amount of inorganic phosphorus released by adding the bean meal and the purified phytase variant to the artificial simulation gastric juices, incubating for 1 hour in the water bath shaker is measured (Huang et al., Appl Microbiol Biotechnol. 2008, 80(3):417-26.).

Furthermore, the present invention also relates to the use of said phytase variants in preparation of the feed additive, and the prepared feed additive. The effective ingredient of said feed additive may be said phytase variants, the host cell expressing the said phytase variants. And, said feed additive may be the dry powder or the liquid preparation, additional containing one or more enzyme products which include, but are not limited to the keratinase, the lipase, the amylase, the phosphatase, the maltase, the convertase, the xylanase, and the carboxymethyl cellulose. Besides the phytase and/or the microorganism producing the phytase, the feed additive of the present invention include other nonpathogenic beneficial microorganisms which include, but are not limited to the probiotic lactic acid Bacteria, the Bifidobacterium, the Yeast helpful to the digestion and absorption of feed, the *Aspergillus oryzae* helpful to the weight gain, the *Bacillus subtilis* capable of producing the useful protease.

BRIEF DESCRIPTIONS OF THE DRAWINGS

EMBODIMENT

Figure 1:
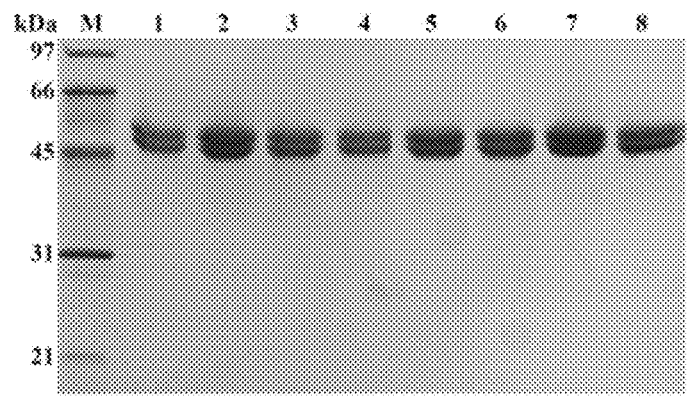
FIG. 1 shows SDS-PAGE electrophoresis of the different purified deglycosylated phytase variants responding to the two electrophoresis strips.

Example 1, Designing the Introduction of the Proline to Obtain the Phytase Variants, Constructing the Expression Vector of the Phytase Variant Gene and Expressing in *Pichia pastoris*

(1) Rational Design the Phytase

A three-dimensional model is researched based on the three-dimensional structure of phytase APPA of *E. coli* recorded in Protein Databank (http://www.rcsb.org/pdb/). B-factor of the protein is an important indicator of the stability of it specific amino acid, which the higher B-factor value of the amino acid, and the lower structure stability of said amino acid or the section containing it. Finally, the sites of the phytase APPA with higher flexibility are determined as S80, S151, T161, N176, S187 and A380 by calculating and ranking the B-Factor value of each amino acid, optimizing based on the research on the amino acid and the section containing it with the higher B-Factor value in connection with the assay results. Then, the prolines are introduced at these sites so as to increase the rigidity of said section and further improve the phytase's thermostability.

(2) Expressing the Phytase Variants:

Site-directed mutagenesis is performed with DpnI digestion and homologous recombination, using only two mutation primers, and constructing the mutant molecules taking 4 hours, which is quicker and more convenient than Overlap PCR. The mutant genes being confirmed by sequencing are correctly inserted into the downstream of the signal peptide of pPIC9 (Invitrogen, San Diego, Calif.) at the EcoRI and NotI sites to construct the correct ORF, and the yeast expression vectore having been constructed is transformed into JM109 cells. 8 μg of the extracted plasmid DNA is linerized with BglII, followed by being transformed into *Pichia* GS115 by electroporation. The transformed cells are plated in Histidine deficient RDB agar medium and cultivated at 30° C. for 2 to 3 days to obtain the transformants for the further expression assay.

(3) Screening the Transformants with High Phytase Activity

The transformants on the RDB plate are picked, numbered and transferred to MM plate and MD plate respectively, placing in the incubated at 30° C. for 1-2 days until growing the colony. The transformants on the MD plate are picked in the numbering sequence, and inoculated into 3 mL of BMGY medium in the centrifuge tube, placing in the shaker with the rate of 260 rpm at 30° C. for 48 hours, followed by spinning down (3000 g, 15 min) to remove the supernatant and being suspended in 1 mL of 0.5% methanol medium (BMMY) to induce the expression of the phytase gene at 30° C. and 260 rpm. After 48 hours, the supernatant is obtained by centrifugal (3000 g, 5 min), for measuring the phytase activity to screen the transformant with the highest activity.

Example 2, Preparing the Phytase Variants and Measuring their Activity (1) Concentrate 3 L of supernatant is collected by centrifugal the BMMY medium after induced the expression of the phytase at 4° C. at the rate of 10,000 rpm for 10 mm, concentrated to 250 mL, and further concentrated in a Filtron ultrafiltration unit with 5 kDa cutoff filters to 50 mL;

(2) Ammonium Sulfate Fractionation Precipitation

The concentrated crude phytase is precipitated with the concentration of 40-75% ammonium sulfate, and the very low phytase activity is remained in the supernatant at 75% saturation. The precipitant collected by centrifugal is dissolved in 5 mL of Tris-HCl buffer solution with pH 8.0, and dialyzed, followed by concentrating with PEG 8000.

(3) Anion Exchange Chromatography

The dialyzed phytase is purified with HiTrap Q Sepharose XL, anion exchange chromatography column, equilibrated with 20 mmol/L Tris-HCl solution (pH 8.0), eluted with 20 mmol/L Tris-HCl solution (pH 8.0) containing 1 mol/L NaCl, and loaded with 2 mL of phytase, followed by linear gradient eluting at 0-100% at rate of 4 mL/min, and fractionally collecting the peak to obtain the interest protein with a molecular weight of about 48-53 kDa and a purity more than 95% having been purified by SDS page, as shown in FIG. 1. The protein concentration of the purified phytase is measured with the Bradford method.

(4) Mearing the Phytase Activity

The purified phytase is diluted with 0.25 mol/L NaAc-HAc containing 0.05% BSA, and 0.05% Triton X-100 (pH 4.5), and 50 μL of diluted phytase solution is added to 950 μL substrate of 1.5 mmol/L sodium hyaluronate (0.25 mol/L sodium phytase (pH 4.5) in 1.5 mmol/L sodium acetate buffer (Sigma Cat. No. P0109)), kept at 37° C. for 15 mm, followed by adding 1 mL of 10% (m/v) TCA to stop the reaction, and 2 mL of color reagent. Then, OD is measure at 700 nm to calculate the phytase activity. 1 unit of phytase activity is determined to be the enzyme amount releasing 1 μmol of phosphate for 1 minute. The absolute value of the measured phytase activity may be calculated based on the standard curve of inorganic phosphate in dilution.

Example 3, Optimal Temperature and Thermostability of the Phytase Variants (1) Temperature Characteristic The activity of the interest dilution of the phytase variants purified in the Example 2 is measured in 0.25 mol/L sodium acetate buffer (pH 5.5) from 30° C. to 90° C., followed by calculating the specific activity as the average of three measurements repeated at each temperature, so as to determine the optimal temperature of said phytase, as list in the table 1 showing the mean of the specific activity at each temperature.

TABLE 1

| Phytase Variants | Reacting temperature ( 0-100 meaned in relative activity and 100 stand for the optimum temperature of the variant) | | | | | | | | |
|---|---|---|---|---|---|---|---|---|---|
| | 30° C. | 40° C. | 50° C. | 60° C. | 70° C. | 75° C. | 80° C. | 85° C. | 90° C. |
| Appa-WT | 20 | 41 | 68 | 100 | 39 | 18 | 10 | 2 | 0 |
| Appa-A | 20.7 | 34.5 | 53.1 | 76.5 | 100 | 88.5 | 59.6 | 4.9 | 0 |
| Appa-B | 21.8 | 42.3 | 63.7 | 88 | 95.1 | 100 | 66.7 | 7.6 | 0.9 |
| Appa-C | 14.5 | 27.4 | 50 | 71.1 | 91.0 | 98.7 | 100 | 80.2 | 45.3 |

Wherein, specific activity is remarked as 0 to 100, and the temperature with 100 of the specific activity is the optimal temperature.

(2) Determining the Thermostability 2 mL of the interest dilution of the phytase variants purified in the Example 2 is kept for 30 mm at 60° C., 65° C., 70° C., 75° C., 80° C., 85° C., respectively, the phytase sample is taken and placed on the ice when 2 min, 4 min, 10 min, 5 min, 20 min, 30 min to measure the phytase activity of the phytase diluted for 10 times at 37° C. and the optimal pH using the untreated crude phytase as control, so as to determine the optimal temperature of said phytase, as list in the table 1 showing the mean of the specific activity at each temperature, wherein the specific activity is the average of three measurements repeated at each temperature. The thermostability data of the phytase variants with the improved thermostability is shown as FIG. 2.

Figure 2:
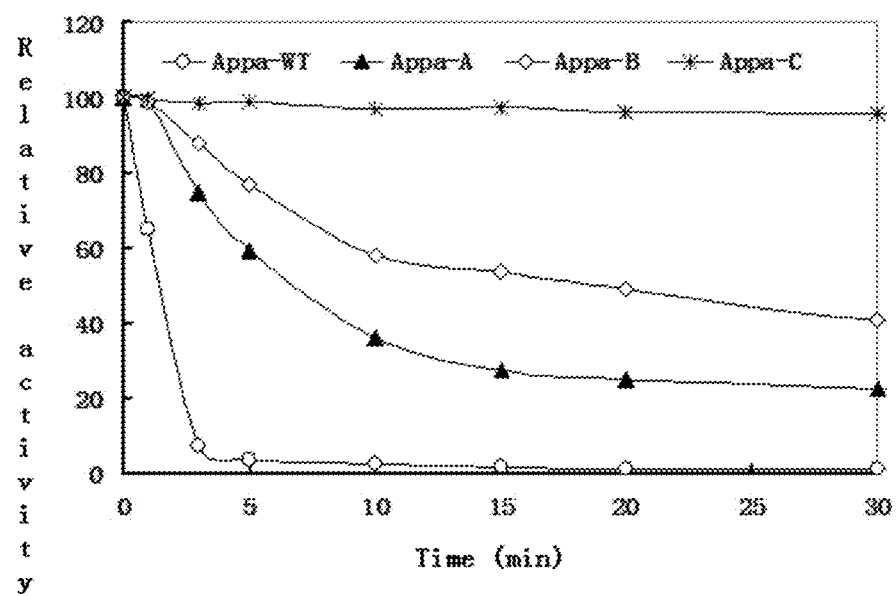
FIG. 2 shows the thermostability of the phytase variants at the temperature of 80° C.

As shown in FIG. 2, the thermostability of several phytase variants is obviously improved, remaining 40% of activity being left at 80° C. for 10 mm, and remaining 25.8% of activity being left at 80° C. for 30 min. In comparison, the specific activity of the wild phytase APPA is high only at 65° C., obviously decreases with the increase of the temperature, almost losing at 80° C. for 2 min. The thermostability of the several phytase variants at 85° C. indicates the resistance to the short high temperature treatment at 80° C. during feed pelleting. The phytase variants show the great potential of industrial application due to their improved thermostability at 80° C. and 85° C.

37° C. for the order of determining effect of proteases on the enzyme activity of the phytase variants. And then, sample incubated was collected respectively at 5 min, 10 min, 20 min, 30 min, 60 mm, 90 mm and 120 min to measure the enzyme activity at 37° C. and pH5.5. The specific activity is calculated, as list in the table 2, with untreated phytase as the control of 100%. As list in the table 2, the phytase variants have the greatly improvement on the trypsin resistance, and little change on the pepsin resistance.

TABLE 2

| Phytase | Pepsin ( Treatment time (min)) | | | | | Trypsin ( Treatment time (min)) | | | | |
| --- | --- | --- | --- | --- | --- | --- | --- | --- | --- | --- |
| variants | 5 | 10 | 30 | 60 | 120 | 5 | 10 | 30 | 60 | 120 |
| Appa-WT | 105.6 | 111.2 | 115 | 116.8 | 117.3 | 59.4 | 45.7 | 43.2 | 39.6 | 35.1 |
| Appa-A | 103.7 | 108.4 | 113.9 | 115.7 | 116.9 | 80.9 | 69.6 | 58.3 | 52.3 | 48.4 |
| Appa-B | 102.2 | 107.2 | 113.3 | 115.1 | 116.2 | 89.3 | 83.4 | 69.9 | 65.3 | 59.2 |
| Appa-C | 101.3 | 106.9 | 110.6 | 113.4 | 115.6 | 97.9 | 90.3 | 84.4 | 76.3 | 69.4 |

Example 4, the Optimal pH and pH Stability of the Phytase Variants

The desalted phytase fermentation supernatant is performed the enzymatic reactions in pH 1.0 to 10.0 using 0.1 mol/L of Glycine-HCl buffer (pH1.0~3.0), acetic acid-sodium acetate buffer (pH3.5~5.5), acetic acid buffer (pH6.0~6.5), Tris-Hcl buffer (pH7.0~8.5) and glycine-sodium hydroxide buffer (pH9.0~10.0) at 37° C. to determine the optimal pH.

The phytase is treated in the different pH buffers at 37° C. for 1 hour, followed by measuring the specific activity in 0.1 mol/L of sodium acetate buffer (pH4.5) at 37° C. in order to research its pH stability.

The optimal pH and pH stability of the phytase variants don't obviously change, and the optimal pH is 4.5, except that the stability and activity of the only part of the phytase variants have been improved under the acidic condition.

Example 5, Measuring the Specific Activity of the Phytase Variants

The protein concentration of the purified phytase variants is determined with Bradford kit for the order of their specific activity. The unit of the specific activity of the recumbent phytase is determined with the molybdenum blue spectrophotometry method at 37° C. and pH 5.5. 1 unit of phytase activity was determined to be the enzyme amount for releasing 1 μmol of inorganic phosphate in 4 mM of sodium phytate (pH5.5) at 37° C. for 1 minute, and the specific activity of the phytase variant may be calculated.

The specific activity of the phytase variants of the present invention ranges from 2500 to 3100 U/mg at 37° C. and pH 5.5, being little different from that of the wild phytase as control, and therefore not being affected with the improvement on their thermostability.

Example 6, Effect of Proteases on the Enzyme Activity of the Phytase Variants 0.1 mg/mL of the purified phytase variants was incubated with 0.01 mg/ml of pepsin and trypsin in equal volume at Example 7, Performance in Animal Feeding and the Simulated Assay In Vitro Further, it is reached the stability and the hydrolytic ability for the phytate of the purified phytase variant in the artificial simulation gastric juices, in order to compare the degradation ability to the phosphorus in the beat meal of the phytase variants with wild phytase as control in the artificial simulation gastric juices.

(1) The Stability of the Phytase Variants in the Artificial Simulation Gastric Juices The remained phytase activity is measured respectively at the optimal pH by adding the same units of phytase variants to the artificial simulation gastric juices until the concentration of the phytase is 1 U/mL, followed by keeping at 37° C. for 20 mm, showing the control wild phyase having the 30% of relative activity remained, and the phytase variants of the present invention having the remaining relative activity more than 70% after one hour's treatment in the artificial simulation gastric juices. Therefore, the phytase variants with the improve thermostability have the more stable structure so as to be capable of resisting to the strong acid and the hydrolysis of the high concentration of the protease.

(2) The Hydrolytic Ability for the Phytate of the Purified Phytase Variant in the Artificial Simulation Gastric Juices 1 g of the bean meal is dissolved in 9 mL of the artificial simulation gastric juices, followed by keep shaking for 1 hour at 37□, respectively adding 1 mL of phytase variants and control diluted in the artificial simulation gastric juices, under the ice condition and reacting for 1 hour at 37° C. The released inorganic phosphorus is measured to evaluate the hydrolysis of the phytase, and a test of pH gradient cumulative effect is performed in order to further simulate gastro enteric environment, showing that the amount of released the inorganic phosphorus by the several thermal stable phytase variants is increased by 50-300%, being more than that by the control phytase. Therefore, the phytase variants of the present invention with the improved thermostability may more efficiently degrade phytate in the artificial simulation gastric juices, have a prominent application prospect.

The invention claimed is:

1. A method of preparing phytase variants having improved thermostability, including the step of introducing prolines at the sites of S80, S151, T161, N176, S187 and A380 of the phytase with the amino acid sequence set forth in SEQ ID NO:2.

2. Phytase variants having improved thermostability with the following characteristics:
   having prolines introduced at the sites of S80, S151, T161, N176, S187 and A380 of the amino acid sequence set forth in SEQ ID NO:2.

3. A polynucleotide encoding the phytase variants having improved thermostability of claim 2.

4. A nucleotide construct comprising the polynucleotide of claim 3, and optionally a regulating sequence connected to said polynucleotide to guide expression in an expression host.

5. A recombinant expression vector comprising the nucleotide construct of claim 4.

6. A recombinant host cell comprising the recombinant expression vector of claim 5.

7. The recombinant host cell according to claim 6, wherein said host cell is a bacteria cell or a fungal cell.

8. A method of producing a phytase variant having improved thermostability, comprising the steps of:
   (a) cultivating the recombinant host cell of claim 6 to produce a supernatant containing said phytase variant; and
   (b) recovering said phytase.

9. A method of preparing an animal feed, comprising adding one of the phytase variants of claim 2 as a feed additive.

10. A method of preparing an animal feed, comprising using recombinant host cell of claim 6 to manufacture a feed additive.

11. An animal feed, comprising a phytase variant of claim 2 as a feed additive.

\* \* \* \* \*